United States Patent
De Vries et al.

(10) Patent No.: US 10,023,553 B2
(45) Date of Patent: Jul. 17, 2018

(54) METHOD AND DEVICE FOR MANUFACTURING LACTIDE

(71) Applicant: PURAC BIOCHEM BV, Gorinchem (NL)

(72) Inventors: Johannes Jeichienus De Vries, Gorinchem (NL); Ana Isabel Cavaco Morao, Gorinchem (NL); Andre Banier De Haan, Gorinchem (NL)

(73) Assignee: PURAC BIOCHEM BV, Gorinchem (NL)

( * ) Notice: Subject to any disclaimer, the term of this patent is extended or adjusted under 35 U.S.C. 154(b) by 0 days.

(21) Appl. No.: 15/570,244

(22) PCT Filed: Apr. 28, 2016

(86) PCT No.: PCT/EP2016/059539
§ 371 (c)(1),
(2) Date: Oct. 27, 2017

(87) PCT Pub. No.: WO2016/174161
PCT Pub. Date: Nov. 3, 2016

(65) Prior Publication Data
US 2018/0155313 A1    Jun. 7, 2018

(30) Foreign Application Priority Data
Apr. 30, 2015  (EP) .................... 15166019

(51) Int. Cl.
| | | |
|---|---|---|
| C07D 319/12 | (2006.01) | |
| B01D 3/34 | (2006.01) | |
| B01D 3/42 | (2006.01) | |
| B01J 19/00 | (2006.01) | |

(52) U.S. Cl.
CPC ............. *C07D 319/12* (2013.01); *B01D 3/34* (2013.01); *B01D 3/42* (2013.01); *B01J 19/0013* (2013.01); *B01J 19/0066* (2013.01); *B01J 2219/00033* (2013.01); *B01J 2219/00051* (2013.01); *B01J 2219/00166* (2013.01)

(58) Field of Classification Search
CPC ................................................... C07D 319/12
USPC ......................................................... 549/274
See application file for complete search history.

(56) References Cited

U.S. PATENT DOCUMENTS

| | | | |
|---|---|---|---|
| 5,288,881 A | | 2/1994 | Drysdale et al. |
| 5,521,278 A | * | 5/1996 | O'Brien ............... C07D 319/12 528/354 |
| 2012/0116100 A1 | * | 5/2012 | Kamikawa ........... C07D 319/12 549/274 |

FOREIGN PATENT DOCUMENTS

| | | |
|---|---|---|
| EP | 0 893 462 A2 | 1/1999 |
| WO | 93/15127 A1 | 8/1993 |

OTHER PUBLICATIONS

Jul. 25, 2016 International Search Report issued in International Patent Application No. PCT/EP2016/059539.
Jul. 25, 2016 Written Opinion of the International Searching Authority issued in International Patent Application No. PCT/EP2016/059539.

* cited by examiner

*Primary Examiner* — Nizal S Chandrakumar
(74) *Attorney, Agent, or Firm* — Oliff PLC

(57) ABSTRACT

A method and a device for manufacturing lactide, whereby crude lactide, being prepared by means of depolymerization of lactic acid oligomers, is purified by means of a distillation step. The prepared crude lactide is maintained for a period of at least 5 hours in a reaction vessel at a temperature between 97° C. and 200° C. prior to the distillation step. Keeping the lactide during a period of time in a reaction vessel leads to a decrease of the lactic acid content and an increase of the lactic acid oligomer concentration, so that the resulting crude lactide can be more efficiently purified during subsequent distillation. A pre-distilling step gives additional advantages.

10 Claims, 4 Drawing Sheets

METHOD AND DEVICE FOR MANUFACTURING LACTIDE

The invention relates to a method for manufacturing lactide, wherein crude lactide, being prepared by means of a depolymerization of lactic acid oligomers, is purified by means of a distillation step. The invention also relates to a device for manufacturing lactide comprising a lactide reactor for depolymerization of lactic acid oligomers into lactide, from which reactor a pipeline for transporting the lactide is guided to a distillation column.

The dimeric cyclic ester of the hydroxycarboxylic acid lactide (1,4-dioxane-3,6-dimethyl-2,5-dione), sometimes also referred to as dilactide, can be used as a precursor or intermediate compound in the manufacture of high molecular weight polylactic acid (PLA) or PLA-like co-polymers. These polymers may be useful in biomedical and other applications on account of their ability to be degraded biologically and hydrolytically while forming physiologically and environmentally acceptable degradation products.

A method of the type described in the opening paragraph is known as such, for example from EP 0 893 462 A2. For instance, FIG. 2 of this document schematically shows a lactide production method, in which lactide is prepared from lactic acid oligomers in the presence of a catalyst in a lactide reactor 60. The crude lactide formed in this manner is subsequently guided via a pipeline 58, a condenser 72, a further pipeline 74, a fluid transfer system 76 and an even further pipeline 78 to a distillation column 80. In this distillation column, the crude lactide is purified from impurities like water, lactic acid, lactoyl lactate and other possible condensation reaction byproducts.

WO93/15127, which is the parent application of EP 0 893 462 A2 discussed above, describes a continuous depolymerisation step, wherein lactide is continuously removed from the process in the form of a vapour. The crude lactide may be fed directly to a distillation system as a vapour for purification, but it can also first be condensed. The condensed lactide is preferably fed directly to a distillation system for purification. Condensed crude lactide may also be transferred via a fluid transfer mechanism to a distillation system.

U.S. Pat. No. 5,288,881 describes a process wherein crude lactide is manufactured through a depolymerisation process, wherein a crude lactide vapour is condensed, the condensate is solidified by cooling at −10° C. and stored overnight, and the frozen condensation product is liquefied and distilled.

US2012/0116100 describes a process wherein crude lactide is formed through depolymerisation, and transferred in gaseous form to a distillation column via a catch pot. In the catch pot the crude lactide seems to separate into lactide, which is removed from the top of the catch pot and provided to the distillation column, and a residue generated in the depolymerisation process which is withdrawn from the bottom of the catch pot.

The present inventors have found that the known system, although generally working satisfactorily, still suffers from certain disadvantages. In practice it has been shown that the separation of certain volatile components from the desired lactide during the distillation step is rather cumbersome. This holds especially true for the separation of lactic acid from lactide. Removal of the impurity lactic acid from the freshly prepared lactide is highly desired; this impurity may negatively influence polymerization processes executed with lactide. Purified lactide for polymerization preferably has an acid content of less than 10 milli-equivalents per kg (meq/kg), preferably less than 5 meq/kg and more preferably less than 2 meq/kg. Additionally, separation of lactide-coloring substances from the crude lactide by means of distillation has also been shown to be difficult in practice. It has been shown that such substances can be present in freshly prepared crude lactide. Their presence is felt as a disadvantage.

It is an object of the present invention to provide a method for the manufacture of lactide, in which at least one of the mentioned or other disadvantages has been eliminated, mitigated or at least diminished. The invention also aims at providing a device for manufacturing lactide suitable for implementation of the method according to the invention.

These and/or possible other objects of the present invention have been achieved by means of a method for manufacturing lactide, wherein crude lactide, being prepared by means of depolymerization of lactic acid oligomers, is purified by means of a distillation step, which method is further characterized according to the invention in that, prior to the distillation step, the prepared crude lactide is maintained for a period of at least 5 hours in a reaction vessel at a temperature between 97° C. and 200° C.

The present invention is based on the insight acquired by the inventors that storage of freshly produced crude lactide in a reaction vessel for a certain period of time results in an increase of the amount of lactic acid oligomers at the expense of the amount of free lactic acid. During distillation of the crude lactide, lactic acid oligomers can be separated more easily from the lactide than lactic acid. When keeping the crude lactide in liquid form for a period of at least 5 hours in a reaction vessel, the amount of lactic acid can be reduced by more than 20% whereas the amount of lactic acid oligomers will increase. The amount of lactide may also reduce in this period. Overall, the manufacturing process of lactide according to the present invention can be more efficient than the one mentioned in the prior art process. During operation of the invented method, reaction of lactic acid essentially causes the formation of lactic acid oligomers. The vessel in which the crude lactide in liquid form is stored for a certain period of time is therefore indicated as a reaction vessel. It is stressed that in principle vessels of all known shape, design or type as disclosed in the prior art can be used within the course of the present invention. Preferred reaction vessels for use in the present invention are discussed below.

Freshly produced liquid crude lactide is most conveniently obtained from lactic acid oligomers (also referred to as PLA-oligomers). These oligomers are prepared by polymerizing lactic acid monomers by means of a polycondensation process under appropriate temperature and pressure conditions, so that lactic acid oligomers of relatively low molecular weight (polymerization degree usually between 6 and 50) are formed. The so-prepared lactic acid oligomers are subsequently heated in a so-called lactide reactor, usually in the presence of a suitable catalyst, as well known in the art. Under proper reaction conditions, the lactic acid oligomers are depolymerized by a process known as 'back-biting', whereby the cyclic ester lactide is formed. The thus-prepared crude lactide may be removed from the lactide reactor, either in liquid form or in vapor form. In case that the crude lactide form is removed as a vapor, such vapor stream is usually converted into a liquid stream by condensing it on a condenser. It is stressed that no solvents other than lactic acid and lactide itself need be used during the production and the purification of lactide ('solvent-less' or 'neat' process).

In one embodiment, the lactide provided to the reaction vessel where it will be maintained for a period of at least 5 hours has a lactide content in excess of 80 wt. %, preferably in excess of 90 wt. %, more preferably in excess of 95 wt. %. It may optionally comprise minor amounts of lactic acid, lactoyl lactate, water, lactic acid oligomers and/or other possible impurities.

The lactic acid oligomers formed in the reaction vessel may be recycled in the method according to the invention. Preferably the fraction of high boiling lactic acid oligomer residue is removed from the bottom of the distillation apparatus and guided back to the lactide reactor. Said residue may also first be concentrated before being guided to the lactide reactor. The overhead stream, which may be rich in water and/or lactic acid and which may additionally contain some lactoyl lactate, can be fed into an oligomerization reactor for conversion into a depolymerizable lactic acid oligomer (also named: PLA oligomer) as is known in the art. Said lactic acid oligomer may be fed to the lactide reactor for production of lactide. Implementation of such recycles in the method of the invention increases the overall efficiency of the lactide production process.

It is well-known that lactide can exist in three different geometric structures, which have a stereo isomeric relationship. These different structures are distinguished as R,R-lactide (or D-lactide), S,S-lactide (or L-lactide) and R,S-lactide (or meso-lactide). The present invention can be used in the manufacture of all three types of lactides. In practice, the crude liquid streams of crude lactide will contain one of the two lactides selected from D-lactide and L-lactide as a major component. In such stream, meso-lactide will be present as a minor component and the remaining third lactide in an even much smaller amount.

It is a feature of the presently invented method to manufacture lactide that the lactide is maintained for a period of at least 5 hours, more preferably of at least 10 hours in the reaction vessel. Experiments have shown that under these conditions, the amount of lactic acid in the liquid crude lactide stream may be reduced to less than 65% (after 5 hours) and even to less than 50% (after 10 hours) of the original lactic acid concentration present in the freshly prepared crude lactide at the moment of entering the reaction vessel. The maximum time for maintaining the lactide in the reaction vessel is not critical. A value of 120 hours may be mentioned as maximum.

In one embodiment of the present invention, the lactide is agitated, e.g., by stirring, during at least part of the time in which it is maintained in the reaction vessel. Agitation has the advantage that separation of the various compounds in the mixture, in particular lactide and lactic acid oligomers, is reduced. It is preferred for the lactide to be agitated for at least 50% of the maintenance time, in particular for at least 70%. In one embodiment, the lactide is agitated during the entire maintenance period.

Another interesting embodiment of the method according to the present invention has the feature that the reaction vessel is designed as a continuous stirred-tank reactor. Such tank reactor, also known as back-mix reactor, allows for an optimal mixing of the crude lactide stream while certain of its constituents, especially lactic acid, are allowed to react during a certain period of time under given pressure and temperature conditions.

A further embodiment of interest in the invented method of lactide manufacture has the feature that the reaction vessel is designed as a series of at least two continuous stirred-tank reactors, and that the crude lactide is transported through this series of reactors. Experiments have shown that, while using the same conditions of residence time, pressure and temperature, a higher conversion of the monomeric lactic acid and water can be achieved with this embodiment of the invented method. Thus, using this special embodiment of the invented method may result in the need of a smaller reactor volume as compared with an embodiment in which a single stirred-tank reactor is used. The maximum for the number of stirred tank reactors is not critical. A value of 15 reactors may be mentioned as suitable maximum.

Also of interest is the embodiment of the invented method in which the reaction vessel is designed as a plug flow reactor. Such a reactor could be designed as a wide tube vessel through which the liquid lactide is guided, preferably from one end of the tube vessel having an inlet for the crude liquid lactide to the other end of the tube vessel having an outlet for said crude liquid lactide. The plug flow reactor may be provided with heating means to maintain the lactide flowing through it at a desired temperature at which the lactide is liquid. The tube may have a circular through section, but may also have a different shape. In principle, any reaction vessel design described in the art that may approach plug flow can be used in this embodiment of the invented method. If a plug flow reactor is used, static mixing elements can be present therein to obtain agitation of the lactide.

Also interesting is the embodiment of the method according to the present invention which has the characteristic that the crude liquid lactide is kept or maintained in the reaction vessel under ambient pressure. It is stressed that the method of the invention in principle does also function well using conditions in which the lactide is kept at higher and/or lower pressures, more particularly in the range between 1 mbar and 10 bars. It has however been shown that decreasing or increasing the applied pressure does not result in significant improvements of the method according to the present invention. Therefore, using the method at ambient pressure is strongly preferred for reasons of simplicity and costs.

In the method of the invention the temperature of the lactide in the reaction vessel(s) ranges between 97° C. and 200° C. At temperatures below 97° C., the D-lactide and/or L-lactide present in the liquid crude lactide stream may under certain conditions become solids, so that their flow transport through the various pipelines of the device used in the manufacture of lactide may become problematic. Further, the conversion reactions described above will occur to a lesser extent, if at all, when the lactide is in the solid state. At temperatures above 200° C., undesired polymerization reactions, degradation processes and/or racemization of the freshly prepared lactide may be observed under certain conditions. The temperature range between 100° C. and 150° C. is preferred, as in this range no flow transport problems of the liquid crude lactide are expected. Moreover, no undesired racemization of the lactides can be expected when they are kept below 150° C. In practice, the temperature range between 110° C. and 130° C. has been shown to be optimal for realizing continuous lactide production conditions.

Much interest has also been devoted to the embodiment of the invented lactide production method which is characterized in that a pre-distillation step is performed on the crude lactide between the preparation of the crude lactide and the maintenance of the lactide in the reaction vessel. In this embodiment, the reaction step—during which the unwanted lactic acid in the liquid crude lactide can form lactic acid oligomers—is positioned between two distillation steps. Applying a pre-distillation step on the crude lactide before guiding this crude lactide into said reaction vessel appears to have a positive effect on discoloration of the crude lactide during its purification in the subsequent second distillation step. In this pre-distillation step, water, lactic acid, and volatile contaminants are distilled off, while lactide and higher lactic acid oligomers remain.

An interesting embodiment of the method according to the invention as described in the previous paragraph has the features that the temperature of the lactide in the reaction vessel ranges between 140° C. and 170° C. In view of energy considerations, the process step in the reaction vessel is preferably operated at somewhat higher temperatures as compared with the process not having the additional pre-distillation step.

Also of interest is a method according to the present invention, which is defined by the feature that lactide improving additives are added to the reaction vessel. Attractive additives in this respect are compounds or mixtures of compounds having anti-oxidizing, discoloring or other stabilizing properties. A variety of process stabilizers can be used, either alone or in combination. Preferably, hindered phenolic compounds, or other phenolic compounds may be used as process stabilizing antioxidants. Most preferably, phosphite-containing compounds are used for this purpose. The amount of the additives used can vary. Preferably, amounts of at least about 0.01 wt. % and less than about 1 wt. % are used. More preferably, amounts of at least about 0.025 wt. % and less than about 0.3 wt. % are used.

The invention also relates to a device for manufacturing lactide comprising a lactide reactor for depolymerization of lactic acid oligomers into lactide, from which a pipeline for transporting crude lactide is guided to a distillation column. Such device is characterized according to the invention in that a reaction vessel is provided in the pipeline between the lactide reactor and the distillation column. For reasons described elsewhere in this document, it is preferred to design the reaction vessel as a continuous stirred-tank reactor, whereas it is more preferred that the reaction vessel is designed as a series of at least two continuous stirred-tank reactors. As an attractive alternative, the reaction vessel may also be designed as a plug flow reactor.

Of great interest is an embodiment of the device according to the invention which is characterized in that a second distillation column is provided in the pipeline between the lactide reactor and the reaction vessel. With this device the quality of the produced lactide, including its acidity and especially its color, can be significantly improved.

The present invention is described in more detail and elucidated by different examples and by drawings, without being limited thereto or thereby.

For reasons of clarity, it is stressed that the Figures are presented schematically and not to scale. Identical elements in different Figures are as much as possible referred to with the same reference numbers.

Figure 1:
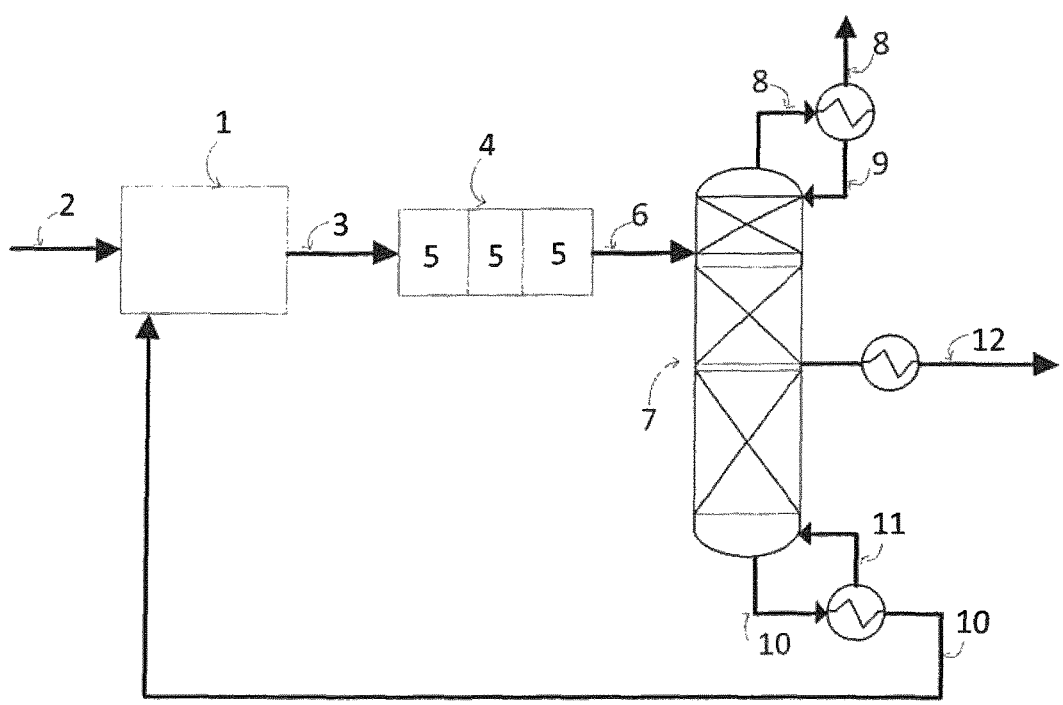
FIG. 1 shows a first embodiment of a device and related method according to the present invention, in which a single distillation column is used.

The method for the manufacturing lactide according to the present invention is explained by means of a device for manufacturing lactide as depicted in FIG. 1. More particularly, this Figure shows a lactide reactor 1 which is fed via pipeline 2 with lactic acid oligomers having a polymerization degree approximately between 6 and 50. From these oligomers, crude lactide is manufactured by means of a ring-closing depolymerization process, which in one embodiment is catalyzed by means of, e.g., tin-octoate at appropriate temperature and pressure, all as known in the state of the art. A stream of crude lactide is directly guided from lactide reactor 1 via pipeline 3 to a reaction vessel 4. In this embodiment, reactor vessel 4 is composed of three continuous stirred-tank reactors 5. Said stream is mainly composed of lactide (in excess of 80 wt. %, preferably in excess of 90 wt. %, more preferably in excess of 95 wt. %), and minor amounts of lactic acid, lactoyl lactate, water, lactic acid oligomers and other possible impurities.

The crude lactide stream derived from lactide reactor 1 may be in liquid form or in vapor form, depending on the temperature and pressure conditions maintained in lactide reactor 1 and in pipeline 3. In case that the lactide stream is in vapor form, a condenser (not shown in FIG. 1) is positioned in pipeline 3 between the lactide reactor 1 and reaction vessel 4. In the condenser, the lactide and possible other components present in the vapor stream are partly or fully condensed on a cold surface. In case that the lactide stream is in liquid form, no condenser need be present in pipeline 3. In view of the described situations, the crude lactide entering the first stirred tank reactor 5 is in liquid form. Using appropriate heating means, the three stirred tank reactors 5 are kept at a temperature of approximately 126° C. and at ambient pressure.

After being maintained for a period of time in each of the stirred tank reactors 5 of reaction vessel 4, the crude lactide is guided from the last stirred tank reactor via pipeline 6 into distillation column 7. In the present invention, the crude lactide which has been maintained in the reaction vessel for a period of at least 5 hours is provided in its entirety to the distillation column. The reaction vessel is not a separation step. In this column 7 different components of the liquid crude lactide stream are separated via a distillation step. This column 7 has a bottom temperature not higher than 170° C. and a pressure of approximately 50 mbar. Under these conditions, volatile components, like lactic acid, water, lactoyl lactate and a small portion of lactide are removed as low-boiling top-fraction via pipeline 8. Part of this top-fraction is refluxed via pipeline 9 into distillation column 7, whereas the other part of the top-fraction being removed via pipeline 8 is recycled (if desired after dehydration) to a prepolymerization reactor (not shown in FIG. 1), which may be present in the lactide manufacturing device.

A high-boiling bottom fraction is removed from distillation column 7 via pipeline 10. This fraction comprises compounds like lactic acid oligomers, having a boiling point much higher than the boiling point of lactide. A major part of this fraction is returned to column 7 via pipeline 11 whereas a minor part of the fraction is recycled to the lactide reactor 1, if needed after a hydrolysis step and, optionally, after concentration. An intermediate-boiling fraction is removed from distillation column 7 via pipeline 12. Latter fraction comprises lactide in substantially pure form (in excess of 95 wt. %). It is stressed that the lactide present in the pure lactide fraction may be composed of the three stereoisomers L-lactide, meso-lactide and D-lactide. The concentration of these stereoisomers in the pure lactide fraction differ, and is essentially based on the type and optical purity of the lactic acid oligomers and various process conditions applied in the lactide manufacturing process.

It has been shown that the concentration of lactic acid, lactide and lactic acid oligomer in the crude lactide changes in time. More particularly, it has been shown that maintaining or storing the freshly produced crude lactide stream for a period of time results in the increase of its high-boiling fraction and a decrease of its low boiling fraction. Thus, especially, the concentration of lactic acid upstream of the reaction vessel 4 is higher than the concentration of lactic acid downstream from the reaction vessel. Conversely, the concentration of lactic acid oligomer in the crude lactide stream upstream of the reaction vessel 4 is lower than the concentration of lactic acid oligomer downstream from the reaction vessel.

In an initial experiment, a crude lactide fraction was maintained in a reaction vessel for a period of 6 hours at a temperature of approximately 125° C. at ambient pressure. The composition of the crude lactide stream entering the vessel was determined to be 92.8 wt. % L-lactide, 5.5 wt. % meso-lactide 1.2 wt. % of lactic acid and 0.5 wt. % lactic acid oligomer. The composition of the crude lactide fraction leaving the vessel was determined to be 90.8 wt. % L-lactide, 5.4 wt. % meso-lactide, 0.4 wt. % of lactic acid and 3.4 wt. % lactic acid oligomer. Thus, the mass fraction of lactic acid in the liquid crude lactide stream was decreased to approximately 34% of its original amount during the residence time in the reaction vessel. The so-obtained crude lactide stream contained a significantly lower fraction of lactic acid, which results in a much simpler distillation process in column 7, which resulted in lactide with a higher purity.

Figure 2:
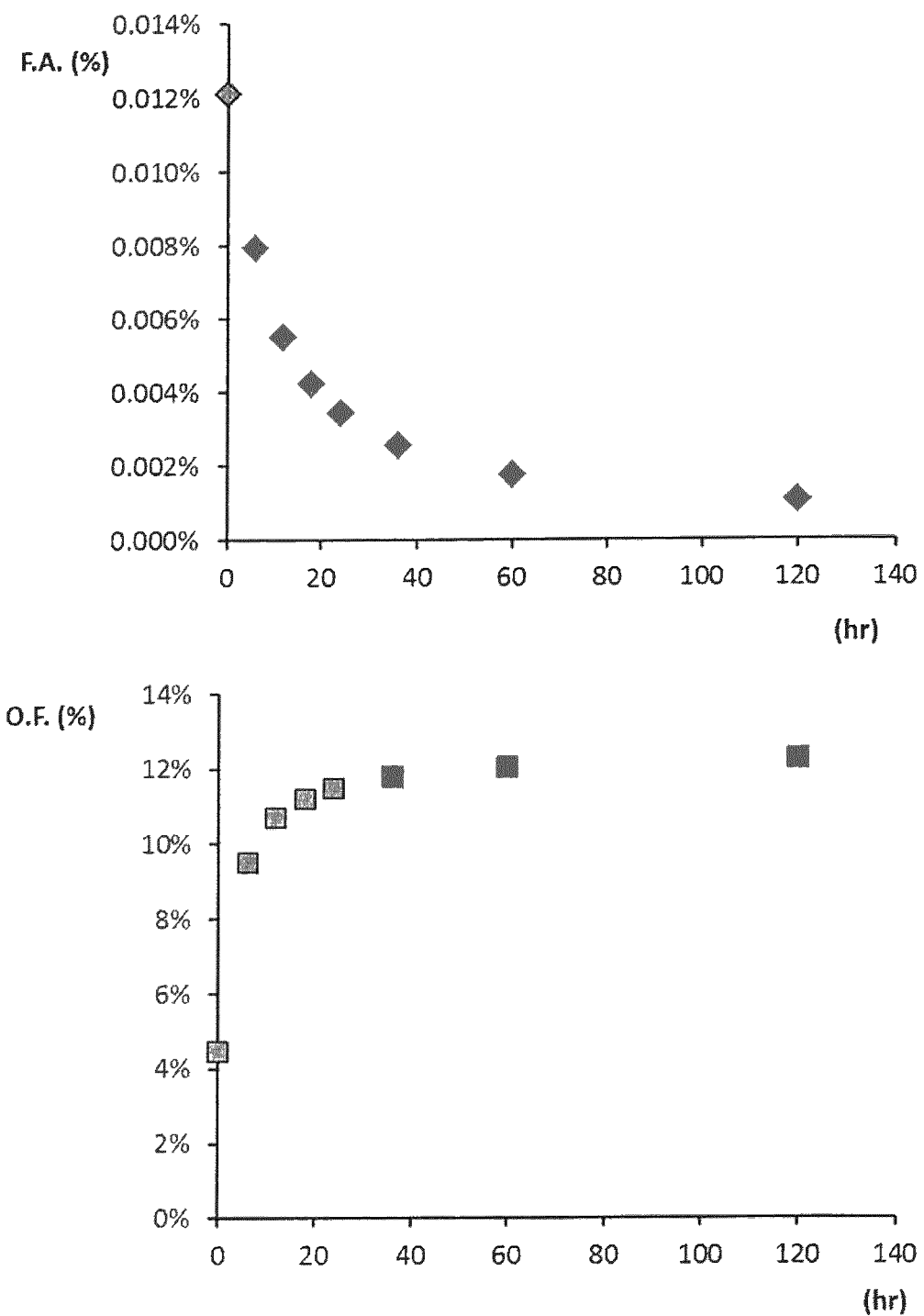
FIG. 2 shows a chart in which the concentration of lactic acid and lactic acid oligomer in the crude lactide is shown as a function of the residence time.

FIG. 2 shows a graph in which the concentration of the lactic acid (F.A., in wt. %) and the concentration of the low-boiling bottom fraction (O.F., in wt. %) in the downstream crude lactide fraction is shown as a function of the residence time in a reaction vessel. In this experiment, a single continuous mixing tank was used for the reaction vessel. The temperature in the tank was 126° C. and the crude lactide was maintained under ambient pressure. The residence time of 0 hr. provides an indication of the concentration of the mentioned impurities in the upstream crude lactide stream, specifically 0.0120 wt. % for the free-acid concentration and 4.2% for the lactic acid oligomer concentration.

This FIG. 2 (bottom) shows the clear trend that increasing the residence time of the crude lactide fraction in the reaction vessel results in an increase of the low-boiling bottom fraction (O.F.), which is substantially composed of lactic acid oligomer material. Storage of the crude lactide for 6 hrs. (second data point from the left) in the reaction vessel results in an increase of the concentration of the low-boiling bottom fraction of more than 100%. Storage of the crude lactide for 40 hrs. in the reaction vessel results in an increase of the concentration of the low-boiling bottom fraction of almost 200%.

This FIG. 2 (top) further shows that increasing the residence time of the crude lactide fraction in the reaction vessel results in a significant decrease of the amount of lactic acid (F.A.), which is substantially identical to the free acid concentration in the crude lactide fraction. Storage of the crude lactide for 6 hrs. (second data point from the left) in the reaction vessel results in a decrease of the concentration of the lactic acid of about 30%. Storage of the crude lactide for 40 hrs. in the reaction vessel results in a decrease of the concentration of the lactic acid of about 70%. These values are well in line with the idea that the lactic acid is converted into lactic acid oligomers, whereby the conversion increases with increasing residence time.

Figure 3:
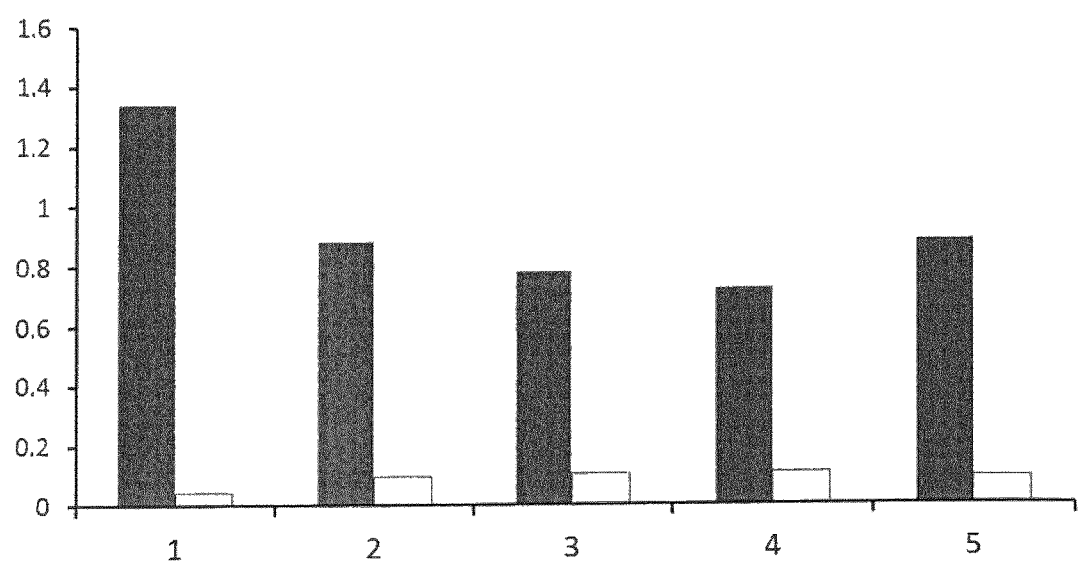
FIG. 3 shows a chart which demonstrates the effect of different reaction vessel designs on the reduction of the lactic acid concentration.

In FIG. 3, the reduction of the lactic acid concentration in the crude lactide fraction (tall bar) as well as the increase of the lactic acid oligomer concentration (adjacent short bar) is measured as a function of various tank designs. The freshly produced crude lactide contained a free acidity of 150 meq/kg, mainly caused by lactic acid. The temperature of the crude lactide in the pipelines and in the reaction vessel, where applicable, was maintained at 126° C. Bars 1 show the situation in which no tank was available. In this reference experiment, the acidity of the transported crude lactide was lowered slightly to approximately 135 meq/kg (bar 1).

Bars 2-5 in FIG. 3 show the effect of the use of a single continuous stirred tank (bars 2), three continuous stirred tanks (bars 3) or ten continuous stirred tanks (bar 4; mimicking plug flow transport) in the method according to the present invention. In these experiments, the crude lactide fraction was kept for 6 hours in each of the indicated reaction vessel designs at 126° C. under atmospheric pressure. From these experiments, it can be concluded that using a reaction vessel indeed causes reduction of the lactic acid or free acid concentration—by comparing tall bars 1 and 2—as well as an increase in the lactic acid oligomer concentration seen by comparing short bars 1 and 2. It can also be concluded that use of a series of continuous stirred tanks gives a higher reduction than the use of a single stirred reaction vessel, and is therefore preferred; tall bars 2, 3 and 4 should be compared in this regard. Best results can be expected with a reaction vessel designed as a plug flow reactor, as mimicked by the design using ten stirred tanks (bar 4). The amount of lactic acid oligomer concentration in the various experiments underlying the results of bars 2-4 appears to be approximately at the same level Bar 5 in FIG. 3 shows the effect of maintaining the crude lactide for 6 hrs. in a single stirred reactor tank at 126° C. under reduced pressure (here at 7.75 mbar). From a comparison of the height of bars 2 and 5, it can be concluded that reducing the pressure does not have a noticeable effect, either on the reduction of the lactic acid amount or on the increase of the lactic acid oligomer concentration.

Figure 4:
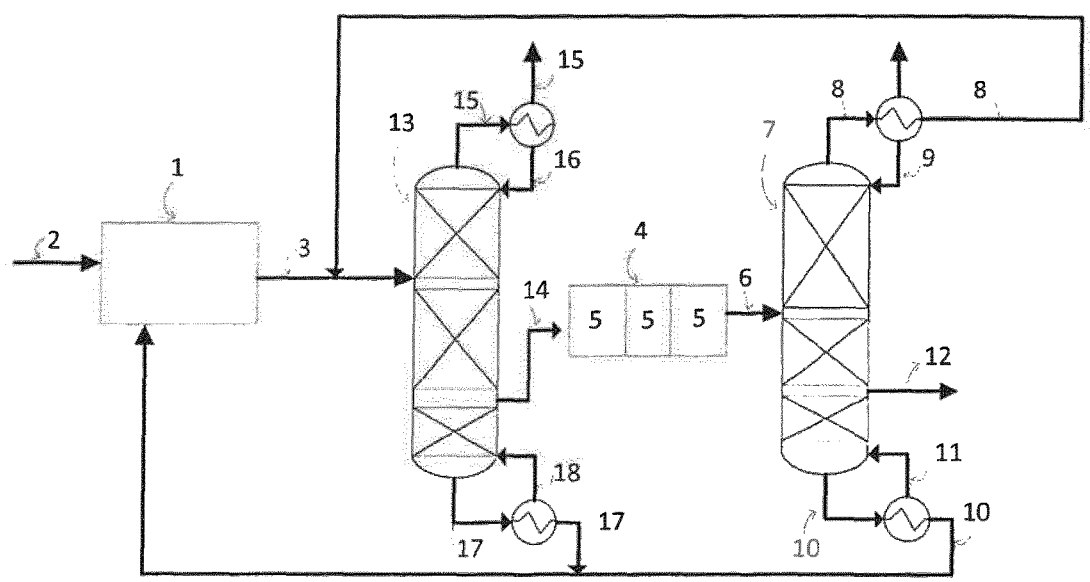
FIG. 4 shows a second embodiment of device and related method according to the present invention, in which two distillation columns are used.

FIG. 4 depicts an alternative process for the production of lactide according to the present invention, in which two distillation columns are used and the reaction vessel is positioned between these two distillation columns. In more detail, this Figure shows a lactide reactor 1 which is fed via pipeline 2 with lactic acid oligomers having a polymerization degree approximately between 10 and 25. From these oligomers, crude lactide is manufactured by means of a ring-closing de-polymerization process. A vapor or liquid stream of crude lactide is directly guided from lactide reactor 1 via pipeline 3 to second distillation column 13, in which different components of the liquid crude lactide stream are separated via a distillation step. This column 13 has a bottom temperature not higher than 170° C. and a pressure of approximately 50 mbar. Under these conditions, volatile components, like lactic acid, water, lactoyl lactate and a small portion of lactide are removed as low-boiling top-fraction via pipeline line 15. Part of this top-fraction is refluxed via pipeline 16 into distillation column 13, whereas the other part of the top-fraction being removed via pipeline 15 may be recycled to a pre-polymerization reactor (not shown in FIG. 4), which may be included in the lactide manufacturing device.

A high-boiling bottom fraction is also removed from distillation column 13 via pipeline 17. This fraction comprises compounds like lactic acid oligomers, having a boiling point much higher than the boiling point of lactide. A major part of this fraction is returned to column 13 via pipeline 18, whereas a minor part may be recycled to the lactide reactor 1, if needed, after a hydrolysis step and, optionally, after concentration.

An intermediate-boiling fraction is removed from distillation column 13 via pipeline 14. Latter fraction comprises lactide in relatively pure form (in excess of 96 wt. %). Said fraction is directly guided to reaction vessel 4. In the present embodiment, reactor vessel 4 is composed of three continuous stirred-tank reactors 5. Said stream is mainly composed of lactide (in excess of 97 wt. %, preferably in excess of 98 wt. %, more preferably in excess of 99 wt. %), and minor amounts of lactic acid, lactoyl lactate, water, lactic acid oligomers and possibly other impurities.

The crude lactide stream derived from distillation column 13 may be in liquid form or in vapor form, depending on the temperature and pressure conditions maintained in distillation column 13 and in pipeline 14. In case that the lactide stream is in vapor form, a condenser (not shown in FIG. 4) is positioned in pipeline 14 between the distillation column 13 and reaction vessel 4. In the condenser, the lactide and possible other components present in the vapor stream are partly or fully condensed on a cold surface. In case that the lactide stream is in liquid form, no condenser need be present in pipeline 14. In view of the described situations, the pre-purified lactide entering the first stirred tank reactor 5 is in liquid form. Using appropriate heating means, the three stirred tank reactors 5 are kept at a temperature of approximately 150° C. and at ambient pressure.

After being maintained for a period of time in each of the stirred tank reactors 5 of reaction vessel 4, the crude lactide is guided from the last stirred tank reactor via pipeline 6 into distillation column 7. In this column 7 different components of the liquid crude lactide stream are separated via a distillation step. This column 7 has a bottom temperature not higher than 170° C. and a pressure of approximately 50 mbar. Under these conditions, volatile components, like lactic acid, water, lactoyl lactate and a small portion of lactide are removed as a low-boiling top-fraction via pipeline 8. Part of this top-fraction is refluxed via pipeline 9 into distillation column 7, whereas the other part of the top-fraction being removed via pipeline 8 is recycled—after dehydration, if desired—to a prepolymerization reactor (not shown in FIG. 1), which may be present in the lactide manufacturing device. The fraction removed via pipeline 8 may be combined with the fraction removed from pipeline 15 to improve the efficiency of the overall process.

A high-boiling bottom fraction is removed from distillation column 7 via pipeline 10. This fraction comprises compounds like lactic acid oligomers, having a boiling point much higher than the boiling point of lactide. A major part of this fraction is returned to column 7 via pipeline 11, whereas a minor part is recycled to the lactide reactor 1, if needed after a hydrolysis step and, optionally, after concentration. The fraction removed via pipeline 10 may be combined with the fraction removed from pipeline 17 in order to improve the efficiency of the overall process.

An intermediate-boiling fraction is removed from distillation column 7 via pipeline 12. Latter fraction comprises lactide in substantially pure form (in excess of 99 wt. %). It is stressed that the lactide present in the pure lactide fraction may be composed of the three stereoisomers L-lactide, meso-lactide and D-lactide. The concentration of these stereoisomers in the pure lactide fraction differ, and is essentially based on the type and optical purity of the lactic acid oligomers and various process conditions applied in the lactide manufacturing process.

It has been shown that the presence of the reaction vessel in the device according to the present invention as shown in FIG. 4 has an advantageous effect. More particularly it has been shown that the concentration of lactic acid, lactide and lactic acid oligomer in the crude lactide maintained in this vessel changes in time. Further, it was demonstrated that maintaining or storing the freshly produced crude lactide stream for a period of time results in the increase of its high-boiling fraction and a decrease of its low boiling fraction. Thus, especially, the concentration of lactic acid upstream of the reaction vessel 4 is higher than the concentration of lactic acid downstream from the reaction vessel. Conversely, the concentration of lactic acid oligomer in the crude lactide stream upstream of the reaction vessel 4 is lower than the concentration of lactic acid oligomer downstream from the reaction vessel.

Irrespective whether produced via the device shown in FIG. 1 or the device shown in FIG. 4, the obtained purified lactide removed from distillation column 7 via pipeline 12 may be in vaporous or in liquid form. Removed lactide in vapor state can conveniently be liquefied on a cold surface of a condenser (not shown in FIG. 1 or 4). The lactide in liquid form can be brought in a vessel and stored or transported in said vessel in (partly) liquid state. Alternatively, the liquid lactide can also be converted into solid state, for example by means of flaking on a drum or cooling belt. The resulting particles may be stored or transported in suitable packages, like big bags, etc.

While the invention has been illustrated and described in detail in the foregoing description, such description is to be considered illustrative or exemplary and not restrictive; the invention is not limited to the disclosed embodiments and experiments. Variations to the disclosed embodiments can be understood and effected by those skilled in the art in practicing the claimed invention, from a study of the disclosure and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. Method for manufacturing lactide, whereby crude lactide, being prepared by means of depolymerization of lactic acid oligomers, is purified by means of a distillation step, wherein, prior to the distillation step, the prepared crude lactide is maintained for a period of at least 5 hours in a reaction vessel at a temperature between 97° C. and 200° C.

2. Method according to claim 1, wherein the crude lactide is maintained for at least 10 hours in the reaction vessel.

3. Method according to claim 1, wherein the reaction vessel is designed as a continuous stirred-tank reactor.

4. Method according to claim 3, wherein the reaction vessel is designed as a series of at least two continuous stirred-tank reactors, and that the crude lactide is transported through this series of reactors.

5. Method according to claim 1, wherein the reaction vessel is designed as a plug flow reactor.

6. Method according to claim 1, wherein the crude lactide is maintained in the reaction vessel under ambient pressure.

7. Method according to claim 1, wherein the temperature of the lactide in the reaction vessel(s) ranges between 100° C. and 150° C.

8. Method according to claim 1, wherein a pre-distillation step is performed on the crude lactide between the preparation of the crude lactide and the maintenance of the lactide in the reaction vessel.

9. Method according to claim 8, wherein the temperature of the lactide in the reaction vessel ranges between 90° C. and 200° C.

10. Method according to claim 1, wherein lactide improving additives are added to the reaction vessel.

* * * * *